United States Patent [19]

Janssen

[11] 4,072,629

[45] Feb. 7, 1978

[54] REGENERATION OF ALKENE DISPROPORTIONATION CATALYST

[75] Inventor: Frank J. Janssen, Houston, Tex.

[73] Assignee: Shell Oil Company, Houston, Tex.

[21] Appl. No.: 735,580

[22] Filed: Oct. 26, 1976

Related U.S. Application Data

[63] Continuation-in-part of Ser. No. 531,515, Dec. 11, 1974, abandoned.

[30] Foreign Application Priority Data

Dec. 18, 1973 United Kingdom ............... 58480/73

[51] Int. Cl.$^2$ ..................... B01J 21/20; B01J 23/92; C07C 3/62
[52] U.S. Cl. ................. 252/416; 252/411 R; 260/683 D
[58] Field of Search ............................ 252/416, 411 R; 260/683 D

[56] References Cited

U.S. PATENT DOCUMENTS

| | | | |
|---|---|---|---|
| 3,005,781 | 10/1961 | Riordam et al. | 252/416 |
| 3,365,513 | 1/1968 | Heckelsberg | 260/683 D |
| 3,444,262 | 5/1969 | Heckelsberg | 260/683 D |
| 3,579,602 | 5/1971 | Reusser | 260/683 D |
| 3,660,507 | 5/1972 | Reusser | 260/683 D |
| 3,725,496 | 4/1973 | Kobylinski et al. | 260/683 D |
| 3,952,070 | 4/1976 | Nowak | 252/411 R |

*Primary Examiner*—Winston A. Douglas
*Assistant Examiner*—P. E. Konopka

[57] ABSTRACT

Alkene disproportionation catalyst which has become deactivated by the deposition of organic material is regenerated by first contacting the catalyst with low molecular weight alkenes at an elevated temperature to partially remove a portion of the deposited organic material and then contacting the catalyst with an oxygen containing gas at temperatures below 650° C in order to remove substantially all of the remaining deposited organic material.

7 Claims, No Drawings

REGENERATION OF ALKENE DISPROPORTIONATION CATALYST

This application is a continuation-in-part of copending application Ser. No. 531,515 filed Dec. 11, 1974, now abandoned.

BACKGROUND OF THE INVENTION

1. Field of the Invention

This invention relates to a process for regenerating solid disproportionation catalysts by contacting first with alkenes and then with an oxygen containing gas.

2. The Prior Art

The catalytic disproportionation of alkenes is a reaction described, for example, in an extensive review article by G. C. Bailey in "Catalysis Reviews"3 (1), 37–60 (1969). Disproportionation processes are also noted in U.S. Pat. No. 3,365,513 issued Jan. 23, 1968; U.S.Pat. No. 3,444,262 issued May 13, 1969; U.S. Pat. No. 3,579,602 issued May 18, 1971; U.S. Pat. No. 3,660,507 issued May 2, 1972; U.S. Pat. No. 3,725,496 issued Apr. 3, 1973 and U.S. Pat. No. 3,726,930 issued Apr. 10, 1973. A wide variety of solid materials are active disproportionation catalysts, for example supported compounds of titanium, vanadium, chromium, manganese, zirconium, niobium, molybdenum, technetium, ruthenium, rhodium, palladium, tin, hafnium, tantalum, tungsten, rhenium, osmium and iridium. Supported compounds of molybdenum, tungsten and rhenium are most suitable. The disproportionation catalysts may contain one or more alkali metal compounds for suppressing side reactions, such as isomerization and polymerization. Compounds of potassium, rubidium and/or cesium giving an alkaline reaction, in an amount between, for example, 0.5–5% by weight, calculated as alkali metal on the support are used for this purpose.

As a rule the activity of a solid disproportionation catalyst gradually declines during use, and the catalyst, after some time, must be regenerated or replaced by fresh catalyst. When deposition of organic material on the catalyst is the cause of this activity drop, the regeneration can be performed by treating the catalyst with an oxygen-containing gas to burn off the organic material (cf. U.S. Pat. No. 3,365,513, issued Jan. 23, 1968). A disadvantage of this regeneration method is that the catalyst may be damaged as a result of too rapid heating of the catalyst particles of exposing the catalyst to temperatures above about 650° C. It is feasible to avoid the use of these high temperatures by treating the catalyst with a gas having a low oxygen content, for example between 0.5 and 4%v. An example of such a gas is air diluted with a gas inert to the catalyst at regeneration conditions, such as nitrogen, a noble gas or steam. However, this method is energy- and time-consuming. The applicant has found that those problems caused by these prior art methods of catalyst regeneration are minimized when a considerable part of the deposited organic materials are removed by contact with alkenes prior to the burn-off with an oxygen containing gas.

BRIEF SUMMARY OF THE INVENTION

This invention is a process for the regeneration of alkene disproportionation catalysts which have been deactivated by the deposition of organic material by (1) contacting this catalyst with alkenes having from 2 to about 12, preferably from 2 to about 5 carbon atoms per molecule at disproportionation temperature such that part of the deposited organic material is removed, (2) optionally contacting the resulting partially regenerated catalyst with an inert gas at a temperature from about 250° to about 650° C, and then (3) contacting the resulting catalyst with an oxygen containing gas at temperatures below 650° C in order to remove substantially all of the remaining deposited organic materials. The process of this invention minimizes damage to the catalyst caused by the burn-off process.

DETAILED DESCRIPTION OF THE INVENTION

This process is directed to the regeneration of a solid catalyst which has been used in the disproportionation of alkene feeds containing at least a portion of alkenes having carbon number greater than 11, i.e., 12 or more, preferably with at least 30 percent, more preferably 40 percent and even more preferably 50 percent of the alkenes in said feed with carbon numbers of greater than 11, i.e., 12 or more and which has become deactivated by the deposition of organic material by first contacting the catalyst with an alkene or mixtures of alkenes having from 2 to about 12, preferably from 2 to about 5 carbon atoms per molecules at disproportionation temperature and subsequently treating the catalyst with an oxygen-containing gas at temperatures below 650° C.

The invention is based on the finding that certain alkenes (referred to as "regenerating alkenes") are capable of removing part of the deposited organic material. These alkenes have a lower average molecular weight than the feed alkenes and generally have from 2 to about 12 carbon atoms per molecule and preferably from 2 to about 5 carbon atoms per molecule. These alkenes may be straight chain or branched. Suitable examples are: ethylene, propylene, 2-butene, isobutene, 1-pentene, 2-methyl-2-butene and 3-methyl-1-butene. Propylene, 2-butene and mixtures thereof are particularly suitable.

By way of explanation, which is not intended to limit the scope of the invention, it is thought that the deposited organic material contains alkenes which enter into a disproportionation reaction with the regenerating alkenes to form alkenes having a molecular weight lower than that of the deposited alkenes. The alkenes thus formed are at least partly removed from the catalyst, thereby decreasing the amount of organic material deposited on the catalyst. This decrease greatly reduces the risk of too rapid heating of the catalyst particles and prevents temperature increases to values above about 650° C during burn-off.

Whereas it is not strictly necessary to separate the used catalyst from the reactant(s) and product(s) of the disproportionation reaction before the catalyst is contacted with the regenerating alkenes, it is generally considered desirable to separate the catalyst at least from the relatively heavy components of the disproportionation feed. This separation can be conveniently conducted by draining the said heavy components.

The regenerating alkenes are contacted with the used catalyst at disproportionation temperature. This "disproportionation temperature" is defined as a temperature or temperatures falling within the range of temperatures required by the specific catalyst for the disproportionation of alkenes. This temperature depends on the type of disproportionation catalyst used. For many solid disproportionation catalysts the temperature range is well known. Alternatively, this range can readily be determined for the particular catalyst involved by one skilled in the art. The disproportionation temperature within the range of usable disproportionation temperature need not be a single temperature, but may vary as a function of time, either step-wise or continuously.

The process of this invention is in particular suitable for the regeneration of catalysts comprising oxides of molybdenum and of cobalt, supported on alumina, and in this case the regenerating alkenes are preferably contacted with the used catalyst at a temperature between about 75° and about 250° C. Obviously, other disproportionation catalysts may be regenerated as well, for example catalysts containing tungsten oxide on silica, tungsten oxide on alumina and rhenium heptoxide on alumina. A temperature between about 75° and 300° C has been found desirable for catalysts comprising tungsten trioxide supported on alumina. In general temperatures of from about 50° to about 350° C are used with temperatures from about 75° to about 300° C being most desirable, but as noted above the optimum disproportionation temperature will depend on the specific catalyst used.

When the regenerating alkenes are contacted with the used catalyst at a relatively low temperature below, say, 250° C, part of the organic material is removed from the catalyst. To remove more material (possibly including alkenes formed in a reaction in which the regenerating alkenes are involved) and, consequently, to further reduce the content of deposited organic material, it is preferred to subsequently increase the temperature to a value between about 250° and about 650° C, preferably between about 300° and about 450° C. The treatment at the higher temperatures may proceed also in the presence of the regeneration alkenes or preferably in the presence of an inert gas.

After the catalyst has been contacted with the regenerating alkenes and optionally with an inert gas, it is then contacted with an oxygen containing gas at a temperature between about 100° and about 650° C in order to remove substantially all of the remaining deposited organic material. This step is conventional in the art and is accomplished by using a diluent for the oxygen which is inert to the catalyst, as for example, steam, nitrogen argon and the like. The concentration of the oxygen in the oxygen-containing gas need not be a constant as a function of time, but may be suitably increased from zero, or a low value to a high value in order to more precisely control the burn-off temperature.

The extent to which the regenerating alkenes have removed any organic material deposited on the catalyst is ascertained by determination of the amounts of organic material on the catalyst, expressed in % by weight of carbon, before and after the treatment with the regenerating alkenes. When a treatment with an inert gas follows the treatment with the regenerating alkenes, the amount of organic material on the catalyst after the treatment with the inert gas has found to be lower than that of a catalyst treated in an identical manner but using the inert gas instead of the regenerating gas. Examples of inert gases are nitrogen, methane and a noble gas.

The regenerating alkenes are preferably contacted with the used catalyst in the gas phase, but the liquid phase or a mixture of liquid and gas phases is also suitable. Subsequently, any organic material still present on the catalyst is burned off with the aid of an oxygen-containing gas.

The process of this invention is further described by the following illustrative embodiments which are provided for illustration and are not to be construed as limiting the invention.

ILLUSTRATIVE EMBODIMENT I

The experiments described in this illustrative embodiment consist of purification, isomerization and disproportionation of alkenes, followed by regeneration of the used disproportionation catalyst.

The starting material was a mixture of 58% by weight of 1-decene and 42% by weight of a fraction obtained by distillation of an alkene mixture formed by oligomerization of ethylene. This fraction contained all ethylene oligomers in the range of from 18 to 80 carbon atoms per molecule, the molar ratio between the oligomers with $(n+2)$ carbon atoms and those with $n$ carbon atoms being 0.78. This starting material was purified by passing it through a bed of gamma-alumina at a temperature of 100° C and at a weight hourly space velocity of 0.2–0.5 $h^{-1}$. The purified alkenes were passed through a bed of an isomerization catalyst consisting of potassium on gamma-alumina at a temperature of 100° C and at a weight hourly space velocity of 0.3–0.9 $h^{-1}$.

Three reactors were charged with equal amounts of a disproportionation catalyst consisting of molybdenum oxide and cobalt oxide, both supported on gamma-alumina having a specific surface area of about 300 $m^2/g$, a pore volume of 0.56 ml/g and consisting of extrudates with a diameter of 1.5 mm. The catalyst contained 4.6%w of cobalt oxide, calculated as cobalt and 8.5%w of molybdenum oxide, calculated as molybdenum. Before use, the catalyst was activated in nitrogen for 24 hours at a temperature of 525° C. Two of the three charged reactors were filled at a temperature of 125° C with alkenes withdrawn from the isomerization reactor and drained immediately after filling. Then, the two drained beds were washed with 2-methyl heptane for 5 hours at a temperature of 100° C and using a weight hourly space velocity of 1 $h^{-1}$. Subsequently, the washed beds were dried for 10 hours by passing nitrogen with a gas hourly space velocity of 300 $h^{-1}$ through the beds at a temperature of 100° C. Through one of the dried catalyst beds, filled with catalyst A, a mixture of regenerating alkenes, the composition of which is stated in the second column from the left of Table II, was passed, using a gas hourly space velocity of 150 $h^{-1}$. while a starting temperature of 100° C was used. During the passage of the gas the temperature was increased from 100° to 220° C at a rate of 10° C per hour. Then, the mixture of regenerating alkenes was replaced by nitrogen and the temperature increased at a rate of 20° C per hour from 220° to 400° C, applying a gas hourly space velocity of 300 $h^{-1}$. At this space velocity, the temperature was maintained at 400° C for a period of 16 hours. At the end of this period the carbon content of catalyst A was determined. Table I presents the result. The second dried catalyst bed, filled with catalyst B, was treated in the same manner with the exception that nitrogen was used instead of regenerating alkenes. Table I presents the carbon content at the end of this treatment. The experiments with catalysts A and B serve as a reference.

The two reactors filled with catalysts A and B were emptied and refilled with fresh catalyst of the same quantities of the same disproportionation catalyst present in the third reactor. The alkene mixture withdrawn from the bed of the isomerization catalyst was divided into three equal portions and each portion was passed through one of the disproportionation reactors. The disproportionation was performed in each of the three reactors at a temperature of 125° C and a weight hourly space velocity of 2 h$^{-1}$. The reactors were run for 100, 300 and 500 hours, respectively. After these three periods the alkene mixtures withdrawn from each of the reactors contained 24–26%w, calculated an starting material, of n-alkenes with 11, 12, 13 and 14 carbon atoms per molecule. At the end of each of the three runs, the reactors were taken out of service and drained. Then, the three disproportionation catalysts were washed and dried as described above for catalysts A and B. The three dried catalysts were each divided into two equal portions in a nitrogen atmosphere. The portions used for 100, 300 and 500 hours are designated catalysts (a) C and D, (b) E and F and (c) G and H, respectively. Catalysts C, E and G were treated as described for catalyst A, but using a gas hourly spce velocity for the regenerating alkenes of 75 h$^{-1}$ for catalysts C and G. The catalysts D, F and H were treated as described for catalyst B, but using a gas hourly space velocity of 75 h$^{-1}$ for nitrogen for catalysts D and H. Table I presents the carbon contents of catalysts C, D, E, F, G and H at the end of their treatment.

TABLE I

| run time, hours | catalyst | carbon content, % w |
|---|---|---|
| 0 | A | 1.37 |
| 0 | B | 1.62 |
| 100 | C | 1.39 |
| 100 | D | 1.83 |
| 300 | E | 1.63 |
| 300 | F | 2.35 |
| 500 | G | 2.45 |
| 500 | H | 3.87 |

In Table II, second and first columns from the right, the compositions of the gases withdrawn from the reactor containing catalyst C are presented when the regenerating alkenes were passed through the reactor at a temperature between 100° and 110° C and 210° and 220° C, respectively.

TABLE II

| | Composition, % m | | |
|---|---|---|---|
| | Regenerating | Gas withdrawn from the used bed at | |
| Component | alkenes | 100–110° C | 210–220° C |
| ethane | < 0.01 | < 0.01 | 0.06 |
| ethene | 0 | 9.9 | 13.5 |
| propane | 1.65 | 1.57 | 1.67 |
| propene | 89.3 | 60.6 | 57.8 |
| n-butane | 0.01 | 0.01 | 0.04 |
| 1-butene + isobutene | 0 | 0.47 | 3.49 |
| trans-2-butene | 8.2 | 18.4 | 13.3 |
| cis-2-butene | 0.74 | 8.6 | 7.7 |
| 1-pentene | 0 | 0.07 | 0.20 |
| trans-2-pentene | 0 | 0.26 | 1.53 |
| cis-2-pentene | 0 | 0.06 | 0.62 |
| 2-methyl-1-butene | 0 | 0 | 0.02 |
| 2-methyl-2-butene | 0 | 0.09 | 0.12 |

Then, the air to the nitrogen passing over the eight catalysts A through H was adjusted so that the oxygen content gradually increased from 0.5 to 20% and the temperature from 400° to 475° C over a period of at most 12 hours, the burning-off period being adapted to the amount of carbon retained on the catalyst. The catalysts did not contain any carbon at the end of this period.

ILLUSTRATIVE EMBODIMENT II

The experiments described in Illustrative Embodiment I with the catalysts A, B, C, D, E and F were repeated with the following differences:

(1) instead of cobalt oxide and molybdenum oxide, tungsten trioxide was used as the disproportionation catalyst;

(2) the disproportionation catalyst contained 8.1%w tungsten trioxide, calculated as tungsten;

(3) the two experiments at 0 run hours and the four disproportionations were conducted at a temperature of 225° instead of 125° C;

(4) the regenerating alkenes were passed through at a temperature increasing from 200° to 280° C instead of from 100° to 220° C, and using a gas hourly space velocity of 150 h$^{-1}$. Then, the regenerating alkenes were replaced by nitrogen and the temperature increased at a rate of 20° C per hour from 280° to 400° C, applying a gas hourly space velocity of 300 h$^{-1}$.

The n-alkenes with 11, 12, 13 and 14 carbon atoms per molecule were obtained in the same yield as in Example I. Table III presents the carbon contents of the regenerated catalysts. The catalysts C' and E' were regenerated like catalyst A, with regenerating alkenes and nitrogen and the catalysts D' and F' like catalyst B, with nitrogen only.

TABLE III

| run time, hours | catalyst | carbon content % w |
|---|---|---|
| 0 | A' | 1.35 |
| 0 | B' | 1.65 |
| 100 | C' | 1.40 |
| 100 | D' | 1.98 |
| 300 | E' | 1.70 |
| 300 | F' | 2.80 |

ILLUSTRATIVE EMBODIMENT III

The experiments described in Illustrative Embodiment I with the catalysts A, B, C and D were repeated with the following differences:

(1) instead of cobalt oxide and molybdenum oxide, rhenium heptoxide was used as the disproportionation catalyst;

(2) the disproportionation catalyst contained 8.7%w rhenium heptoxide, calculated as rhenium;

(3) the regeneration alkenes were passed through the beds of the catalysts A" and C" at a gas hourly space velocity of 150 h$^{-1}$.

The n-alkenes with 11, 12, 13 and 14 carbon atoms per molecule were obtained in the same yield as in Example I. Table IV presents the carbon contents of the regenerated catalysts. Catalyst C" regenerated like catalyst A, with regenerating alkenes and nitrogen and catalyst D" like catalyst B, with nitrogen only.

TABLE IV

| run time, hours | catalyst | carbon content % w |
|---|---|---|
| 0 | A" | 1.40 |
| 0 | B" | 1.60 |
| 300 | C" | 1.65 |
| 300 | D" | 2.40 |

What is claimed is:

1. A process for the regeneration of solid alkene disproportionation catalysts selected from the group consisting of oxides of molybdenum, cobalt, tungsten, rhenium and mixtures thereof supported on alumina or silica which have been used to disproportionate alkene feeds containing at least thirty percent of the alkenes in said feed with carbon numbers of twelve or more and which catalysts have been deactivated by the deposition of organic material which process comprises first contacting the deactivated catalyst with a regenerating alkene or mixtures of alkenes having from 2 to about 5 carbon atoms per molecule at a temperature of from about 50° to about 350° C and then contacting the catalyst with an oxygen-containing gas at a temperature between about 100° and 650° C.

2. The process of claim 1 wherein the regenerating alkene is selected from the group consisting of propylene, 2-butene and mixtures thereof.

3. The process of claim 2 wherein the catalysts comprise oxides of molybdenum, cobalt, tungsten, rhenium and mixtures thereof supported on gamma-alumina.

4. The process of claim 1 wherein the catalyst is additionally contacted after contact with the regenerating alkenes and prior to contact with the oxygen-containing gas with an inert gas at a temperature of from about 250° to about 650° C.

5. The process of claim 4 wherein the inert gas is nitrogen.

6. The process of claim 5 wherein the regenerating alkene is selected from the group consisting of propylene, 2-butene and mixtures thereof.

7. The process of claim 6 wherein the catalysts comprise oxides of molybdenum, cobalt, tungsten, rhenium and mixtures thereof supported on gamma-alumina.

* * * * *